(12) United States Patent
Solomon et al.

(10) Patent No.: US 8,192,414 B2
(45) Date of Patent: Jun. 5, 2012

(54) CANINE DIAPER

(76) Inventors: Nancy Jean Solomon, Zeeland, MI (US); Rachel Ann Gonzalez, Zeeland, MI (US)

(*) Notice: Subject to any disclaimer, the term of this patent is extended or adjusted under 35 U.S.C. 154(b) by 383 days.

(21) Appl. No.: 12/287,504

(22) Filed: Oct. 9, 2008

(65) Prior Publication Data

US 2010/0094235 A1 Apr. 15, 2010

(51) Int. Cl.
*A61F 13/15* (2006.01)

(52) U.S. Cl. ............ 604/385.01; 604/359; 604/360; 604/346; 604/385.24; 604/385.3; 604/391; 604/387

(58) Field of Classification Search ............ 604/385.01, 604/359, 360, 346, 385.24, 385.3, 391, 387
See application file for complete search history.

(56) References Cited

U.S. PATENT DOCUMENTS

| | | | | |
|---|---|---|---|---|
| 4,372,309 A | * | 2/1983 | Fowler | 604/368 |
| 4,527,991 A | * | 7/1985 | Msarsa | 604/399 |
| 4,813,949 A | | 3/1989 | O'Rourke | |
| 4,996,949 A | | 3/1991 | Wunderman et al. | |
| 5,234,421 A | * | 8/1993 | Lowman | 604/385.09 |
| 5,555,847 A | | 9/1996 | Kelly | |
| 6,142,105 A | | 11/2000 | McKnight | |
| 6,368,313 B1 | | 4/2002 | Howard | |
| 6,895,901 B1 | | 5/2005 | Howard | |

* cited by examiner

*Primary Examiner* — Jacqueline F. Stephens
(74) *Attorney, Agent, or Firm* — King & Partners, PLC

(57) ABSTRACT

A canine diaper, comprising: (a) an outer liner, wherein the outer liner is substantially liquid impermeable; (b) an inner liner, wherein the inner liner is substantially liquid permeable, and wherein the inner liner comprises an outer perimeter secured to the outer liner to enclose a cavity therebetween; (c) a cavity positioned between the inner liner and the outer liner; (d) an absorbent core, wherein the absorbent core is retained within the cavity; and (e) at least one tab which secures the outer liner of the canine diaper substantially around a torso of a dog.

20 Claims, 8 Drawing Sheets

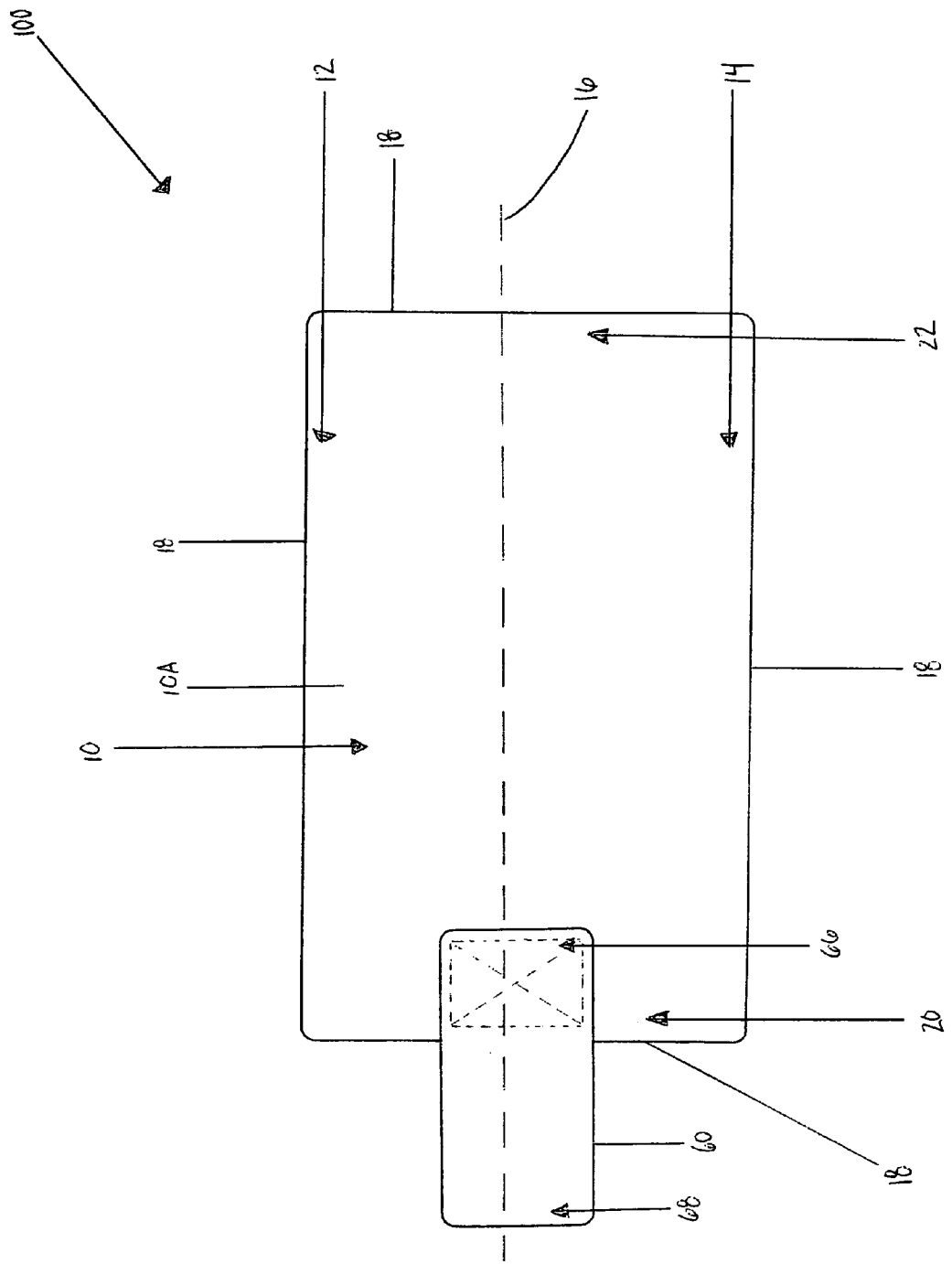

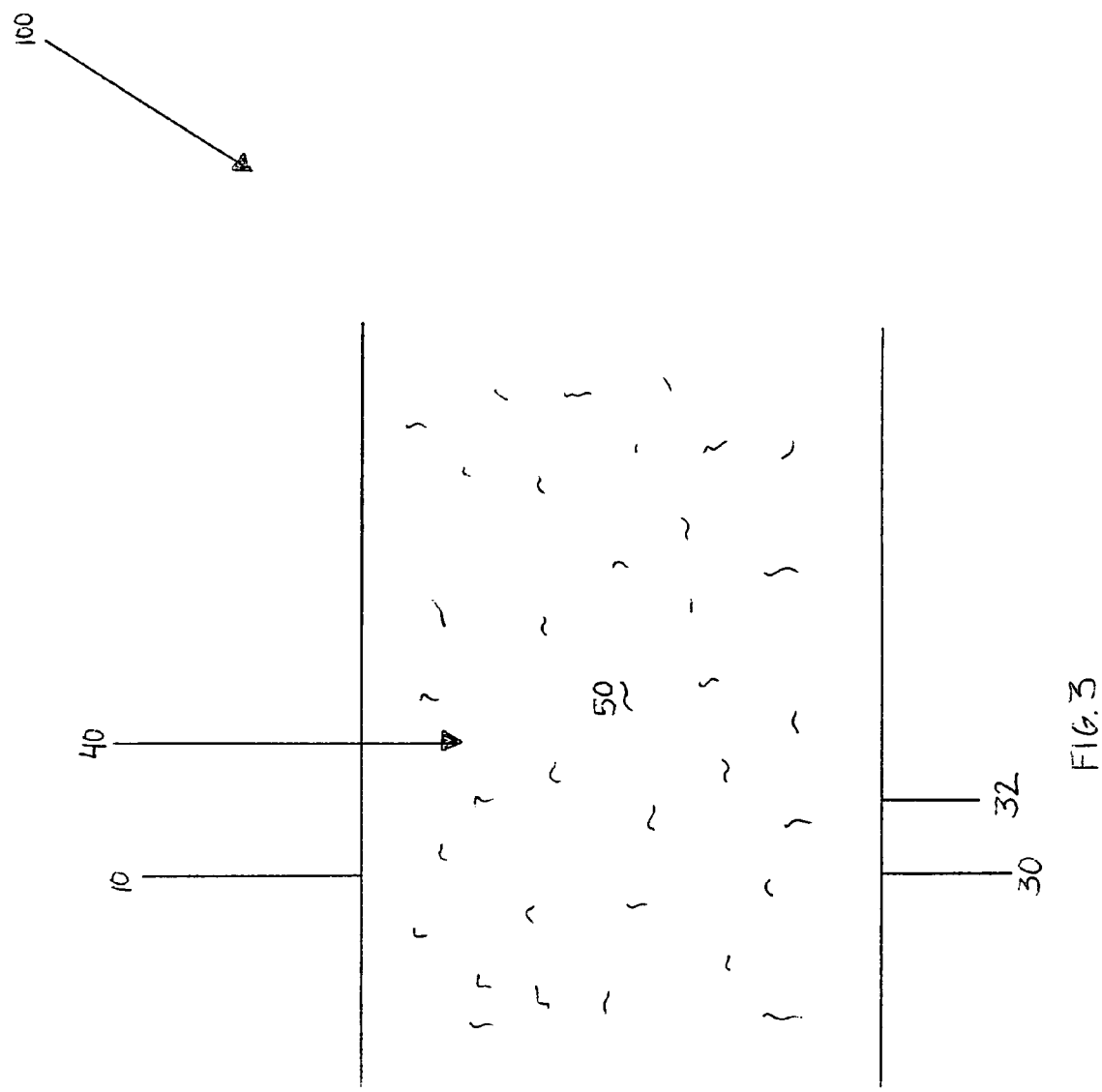

CANINE DIAPER

BACKGROUND OF THE INVENTION

1. Field of the Invention

The present invention relates in general to a canine diaper, and more particularly, to a disposable canine diaper which is easily, securely, and comfortably positionable around a torso of a dog to, in turn, provide a safe, effective, and convenient remedy for canine incontinence.

2. Background Art

Canine diapers have been known in the art for several years. To be sure, canine diapers have gained popularity as an effective remedy for canine incontinence. Typically, canine incontinence occurs as a result of an increased urge to urinate which is uncontrollable by a dog. Such a decrease in the ability to control and resist urine flow is most often due to hormonal, neurologic, anatomical, and/or behavioral reasons.

Canine incontinence can typically be treated via several pharmaceutical medications, including hormone therapy. However, the use of pharmaceutical medications may be disadvantageous for a pet and/or pet owner for a plurality of reasons. First, pharmaceutical medications often require long-term, if not lifetime, administration which can be very costly. In addition, pharmaceutical medications can cause serious side effects, only creating more problems for the pet and pet owner. For these and other reasons, many pet owners desire a non-pharmaceutical remedy for their dog's incontinence.

Canine diapers provide a healthy, effective, and convenient remedy for canine incontinence. However, conventional canine diapers typically require securement of the diaper to a dog by positioning straps and/or openings of the diaper around each of the dog's legs, its tail, and/or its neck. Such a diaper is not only uncomfortable and restrictive for a dog, but it is also difficult and cumbersome for an owner to position on the dog and replace when the diaper becomes soiled.

Another problem associated with conventional canine diapers relates to the manufacturing of the canine diapers. For example, conventional canine diapers typically comprise a plurality of sections, straps, tabs, and specifically placed apertures for accommodating a tail, for example. The plurality of components required to produce a conventional canine diaper increases the cost of manufacturing and, in turn, increases the cost of the diaper for consumers.

U.S. Pat. No. 4,996,949, issued to Wunderman et al. (hereinafter referred to as the '949 patent), which is hereby incorporated herein by reference in its entirety, discloses a disposable dog diaper for removable emplacement and securement circumferentially about a dog's rear torso and his inguinal region. A lower body sheet and upper body wrapper, together with contact adhesive portions, allow such wrap-around emplacement and securement purportedly without slipping, gathering or "bunching up", and, together with removable engagement via the adhesive portions, maximum comfort is afforded to the dog. Highly absorbent material fixedly carried by the body sheet absorbs and retains body fluids, such as urine, discharged by the dog.

However, to the best of Applicant's knowledge, the structure and manufacturing of the disposable dog diaper disclosed by the '949 patent appears to be substantially problematic. To be sure, the disposable dog diaper of the '949 patent is void of a plurality of beneficial structures, functions and/or features which the present invention incorporates to overcome such shortcomings of the '949 patent.

Specifically, the disposable dog diaper of the '949 patent comprises an upper body wrapper, which, to the best of Applicant's knowledge, complicates manufacture of the diaper, thereby increasing the price to consumers. According to the structure disclosed in the '949 patent, the upper body wrapper of the disposable dog diaper is required for securement of the diaper around the dog. To be sure, the upper body wrapper increases manufacturing costs by requiring additional material, size calculations, fusions, and seams, among other difficulties. In comparison, the present invention discloses a canine diaper which is modifiable from mass-produced infant diapers, yet provides securement around a dog which is dependable and comfortable.

Another problem associated with the '949 patent is that the lower body sheet is incapable of fully surrounding the torso of the dog which therefore decreases the security of the diaper around the dog. On the contrary, the outer liner of the canine diaper disclosed herein comprises a first end and a second end, wherein the first end of the outer liner mates with the second end of the outer liner when the outer liner is secured around a torso of a dog via the one ore more tabs (i.e. the at least one tab). This structure greatly increases the security of the diaper around the dog, improving the diaper's prevention of leaks.

In addition, the disposable dog diaper of the '949 patent is completely void of a plurality of beneficial features inherent to the canine diaper disclosed herein, including several features which allow the pet owner to better monitor the integrity of the diaper. For example, the present invention includes a chemical indicator which changes from a substantially colorless state to a highly colored state upon exposure to urine to, in turn, apprise an observer that the canine diaper has been soiled. Additionally, the present invention discloses a urine odor neutralizer and/or an aromatically-pleasing, odor-generating organic ester which masks a natural scent of male canine reproductive organs. Such odor neutralizers and/or esters are impregnated within the diaper to better hide any unpleasant aromas commonly associated with a dog.

Accordingly, it is an object of the present invention to overcome the deficiencies of the prior art and to satisfy the commercial demand for a canine diaper which is easily, securely, and comfortably positionable around a torso of a dog to, in turn, provide a safe, effective, and convenient remedy for canine incontinence.

These and other objects of the present invention will become apparent in light of the present specification, claims, and drawings.

SUMMARY OF THE INVENTION

The present invention is directed to a canine diaper, comprising: (a) an outer liner, wherein the outer liner is substantially liquid impermeable, and wherein the outer liner comprises: (1) a front region, wherein the front region of the outer liner is securable about a front portion of a torso of a dog; (2) a back region, wherein the back region of the outer liner is securable about a rear portion of a torso of a dog; (3) a longitudinal axis; and (4) an outer perimeter which includes a first end and a second end; (b) an inner liner, wherein the inner liner is substantially liquid permeable, and wherein the inner liner comprises an outer perimeter secured to the outer liner to enclose a cavity therebetween; (c) a cavity positioned between the inner liner and the outer liner; (d) an absorbent core, wherein the absorbent core is retained within the cavity; and (e) at least one tab, wherein the at least one tab is substantially parallel to the longitudinal axis of the outer liner, and wherein the at least one tab comprises: (1) a first securement region, wherein at least a portion of the first securement region of the tab is secured directly to the first end of the outer liner; and (2) a second securement region, wherein the second securement region is releasably secured to the second end of the outer liner to, in turn, associate the first end of the outer liner with the second end of the outer liner, thereby securing the canine diaper substantially around a torso of a dog.

In a preferred embodiment of the present invention, the at least one tab comprises at least two tabs. Preferably, the at least one tab consists of two tabs.

In another preferred embodiment of the present invention, all of the first securement region of the at least one tab is secured directly to the first end of the outer liner and within the outer perimeter of the outer liner.

In yet another preferred embodiment of the present invention, the first end of the outer liner mates with the second end of the outer liner when the canine diaper is secured around a torso of a dog via the at least one tab.

Preferably, the second securement region of the at least one tab comprises a fastener which releasably secures the second securement region of the at least one tab to the second end of the outer liner.

It is also preferred that the second securement region of the at least one tab comprises a plurality of hooks, and wherein the second end of the outer liner further comprises a plurality of loops, and wherein the plurality of hooks of the second securement region of the at least one tab releasably secures to the plurality of loops of the second end of the outer liner.

In another preferred embodiment of the present invention, at least one of the front region of the outer liner and the back region of the outer liner comprises a gathered region. Alternatively, it is preferred that each of the front region of the outer liner and the back region of the outer liner comprise a primary gathered region, and the outer liner further comprises two secondary gathered regions positioned within the primary gathered regions.

Preferably, the canine diaper is disposable.

In yet another preferred embodiment of the present invention, the absorbent core comprises at least one of the group comprising: (a) a chemical indicator which changes from a substantially colorless state to a highly colored state upon exposure to urine to, in turn, apprise an observer that the canine diaper has been soiled; (b) a urine odor neutralizer; and (c) an aromatically-pleasing, odor-generating organic ester which masks a natural scent of male canine reproductive organs.

The present invention is also directed to a disposable canine diaper, comprising: (a) an outer liner, wherein the outer liner is substantially liquid impermeable, and wherein the outer liner comprises: (1) a front region, wherein the front region of the outer liner is securable about a front portion of a torso of a dog; (2) a back region, wherein the back region of the outer liner is securable about a rear portion of a torso of a dog; (3) a longitudinal axis; and (4) an outer perimeter which includes a first end and a second end; (b) an inner liner, wherein the inner liner is substantially liquid permeable, and wherein the inner liner comprises an outer perimeter secured to the outer liner to enclose a cavity therebetween; (c) a cavity positioned between the inner liner and the outer liner; (d) an absorbent core, wherein the absorbent core is retained within the cavity; and (e) at least two tabs, wherein each of the at least two tabs is substantially parallel to the longitudinal axis of the outer liner, and wherein each of the at least two tabs comprises: (1) a first securement region, wherein at least a portion of the first securement region of each of the at least two tabs is secured directly to the first end of the outer liner; and (2) a second securement region, wherein the second securement region of each of the at least two tabs is releasably secured to the second end of the outer liner to, in turn, associate the first end of the outer liner to the second end of the outer liner, thereby securing the canine diaper substantially around a torso of a dog.

The present invention is further directed to a disposable canine diaper, consisting of: (a) an outer liner, wherein the outer liner is substantially liquid impermeable, and wherein the outer liner comprises: (1) a front region, wherein the front region of the outer liner is securable about a front portion of a torso of a dog, and wherein the front region of the outer liner comprises a primary gathered region; (2) a back region, wherein the back region of the outer liner is securable about a rear portion of a torso of a dog, and wherein the back region of the outer liner comprises a primary gathered region; (3) two secondary gathered regions positioned within the primary gathered regions; (4) a longitudinal axis; and (5) an outer perimeter which includes a first end and a second end, wherein the first end of the outer liner mates with the second end of the outer liner when the canine diaper is secured around a torso of a dog; (b) an inner liner, wherein the inner liner is substantially liquid permeable, and wherein the inner liner comprises an outer perimeter secured to the outer liner to enclose a cavity therebetween; (c) a cavity positioned between the inner liner and the outer liner; (d) an absorbent core, wherein the absorbent core is retained within the cavity, and wherein the absorbent core at least one of the group comprising: (1) a chemical indicator which changes from a substantially colorless state to a highly colored state upon exposure to urine to, in turn, apprise an observer that the canine diaper has been soiled; (2) a urine odor neutralizer; and (3) an aromatically-pleasing, odor-generating organic ester which masks a natural scent of male canine reproductive organs; and (e) at least two tabs, wherein each of the at least two tabs is substantially parallel to the longitudinal axis of the outer liner, and wherein each of the at least two tabs comprises: (1) a first securement region, wherein all of the first securement region of each of the at least two tabs is secured directly to the first end of the outer liner and within the outer perimeter of the outer liner; and (2) a second securement region, wherein the second securement region of each of the at least two tabs comprises a fastener which releasably secures the second securement region of each of the at least two tabs to the second end of the outer liner to, in turn, associate the first end of the outer liner with the second end of the outer liner, thereby securing the canine diaper substantially around a torso of a dog.

BRIEF DESCRIPTION OF THE DRAWINGS

The invention will now be described with reference to the drawings wherein:

FIG. 1 of the drawings is a top plan (i.e. external) view of an embodiment of a first surface of a canine diaper fabricated in accordance with the present invention;

FIG. 3 of the drawings is a fragmented, cross-section view taken along longitudinal axis 16 showing, among other things, a cavity and an absorbent core, fabricated in accordance with the present invention;

DETAILED DESCRIPTION OF THE INVENTION

Figure 2A:
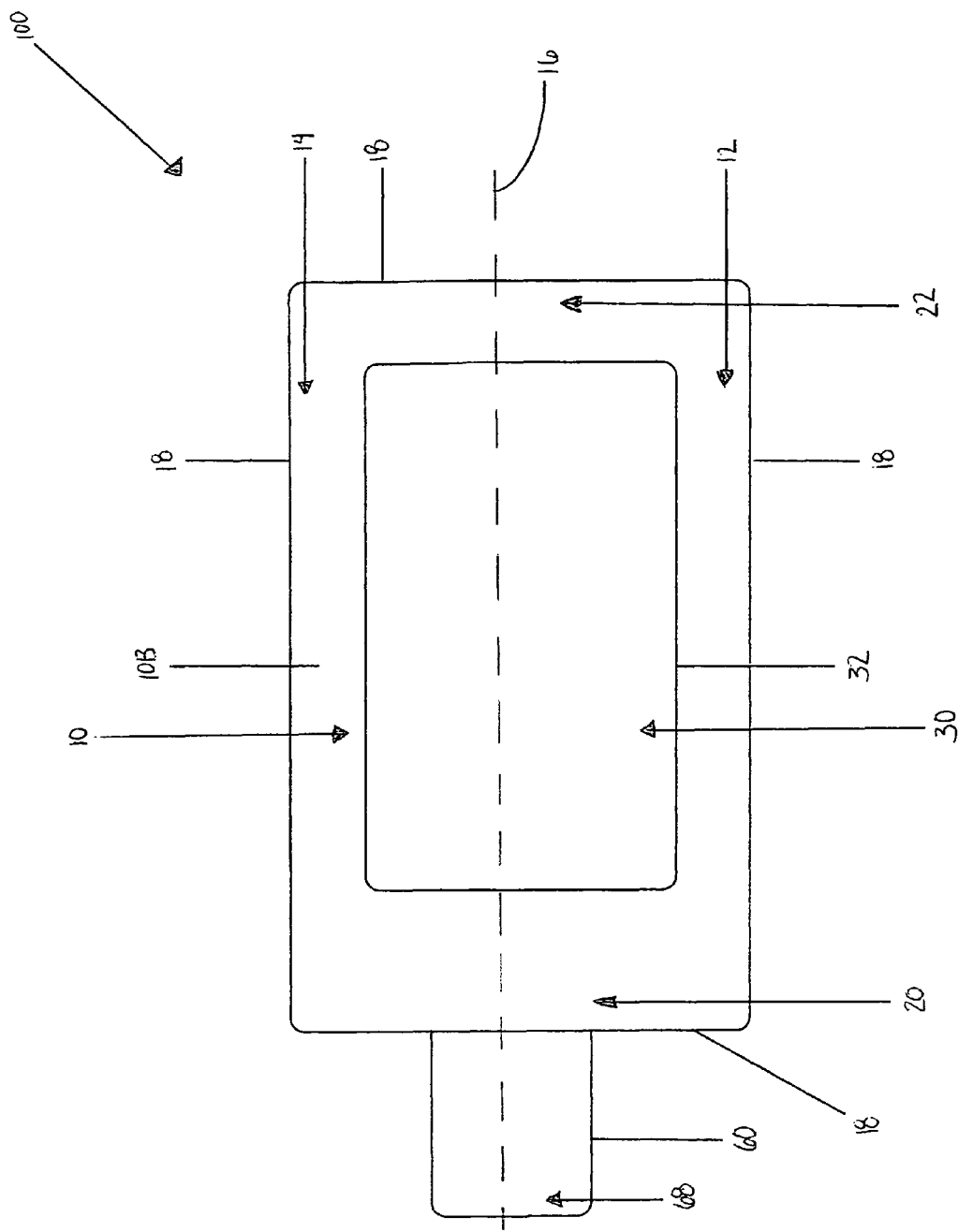
FIGS. 2A-2B of the drawings are bottom plan (i.e. internal) views of embodiments of a second surface of a canine diaper fabricated in accordance with the present invention.

While this invention is susceptible of embodiment in many different forms, there is shown in the drawings and will herein be described in detail specific embodiments with the understanding that the present disclosure is to be considered as an exemplification of the principles of the invention and is not intended to limit the invention to the embodiments illustrated.

Referring now to the drawings and to FIGS. 1-7 in particular, views of canine diaper 100 are shown, which generally comprises outer liner 10, inner liner 30, cavity 40, absorbent core 50, and at least one tab 60. Canine diaper 100 may be disposable or reusable. While canine diaper 100 is shown as having separate members comprising the same or different materials, which are fused, fastened, or otherwise attached, it will be understood that a unitary member is also contemplated. It will be understood that FIGS. 1 through 7 are merely schematic representations of canine diaper 100. As such, some of the components may have been distorted from their actual scale for pictorial clarity.

Outer liner 10 is shown collectively in FIGS. 1-7, among others, as including first surface 10A, second surface 10B, front region 12, back region 14, longitudinal axis 16, outer perimeter 18, first end 20, and second end 22. As is shown in FIGS. 7A and 7B, when canine diaper 100 is positioned on a torso of a dog, first surface 10A of the outer liner is positioned outward and facing away from the dog, and second surface 10B is positioned inward and facing the dog. As is shown in the figures, it is preferred that outer liner 10 comprises a substantially rectangular shape which comprises a size capable of being secured substantially around a torso of a dog. However, it will be understood that outer liner 10 may comprise any one of a number of different shapes and sizes, in order to accommodate the different shapes and sizes of a variety of dogs. Preferably, outer liner 10 is fabricated from a material which is substantially liquid impermeable, flexible, and soft, in order to provide maximum comfort for a dog. It is also preferred that outer liner 10 is fabricated from an elastic, stretchable material. As such, outer liner 10 of canine diaper 100 may be fabricated from, for example, cotton, spandex, plastic, and/or combinations thereof. However, it will be understood that the invention is not limited to a particular material of outer liner 10, and that outer liner 10 may be fabricated from any one of a number of natural and/or synthetic materials.

Front region 12 of outer liner 10 is shown in FIGS. 1-7, collectively, as comprising a region of canine diaper 100 which is securable about at least a lower, front portion of a torso of a dog. As can be seen in FIG. 7A, among others, it is also contemplated that front region 12 of outer liner 10 be securable substantially around a front portion of a torso of a dog. It is preferred that front region 12 comprises primary gathered region 26, as is shown in FIGS. 2B and 4-6, among others. Primary gathered region 26 includes a plurality of gathers or puckers in order for front region 12 to have more flexibility and elasticity which, in turn, provides additional comfort and protection against leaks.

Figure 4:
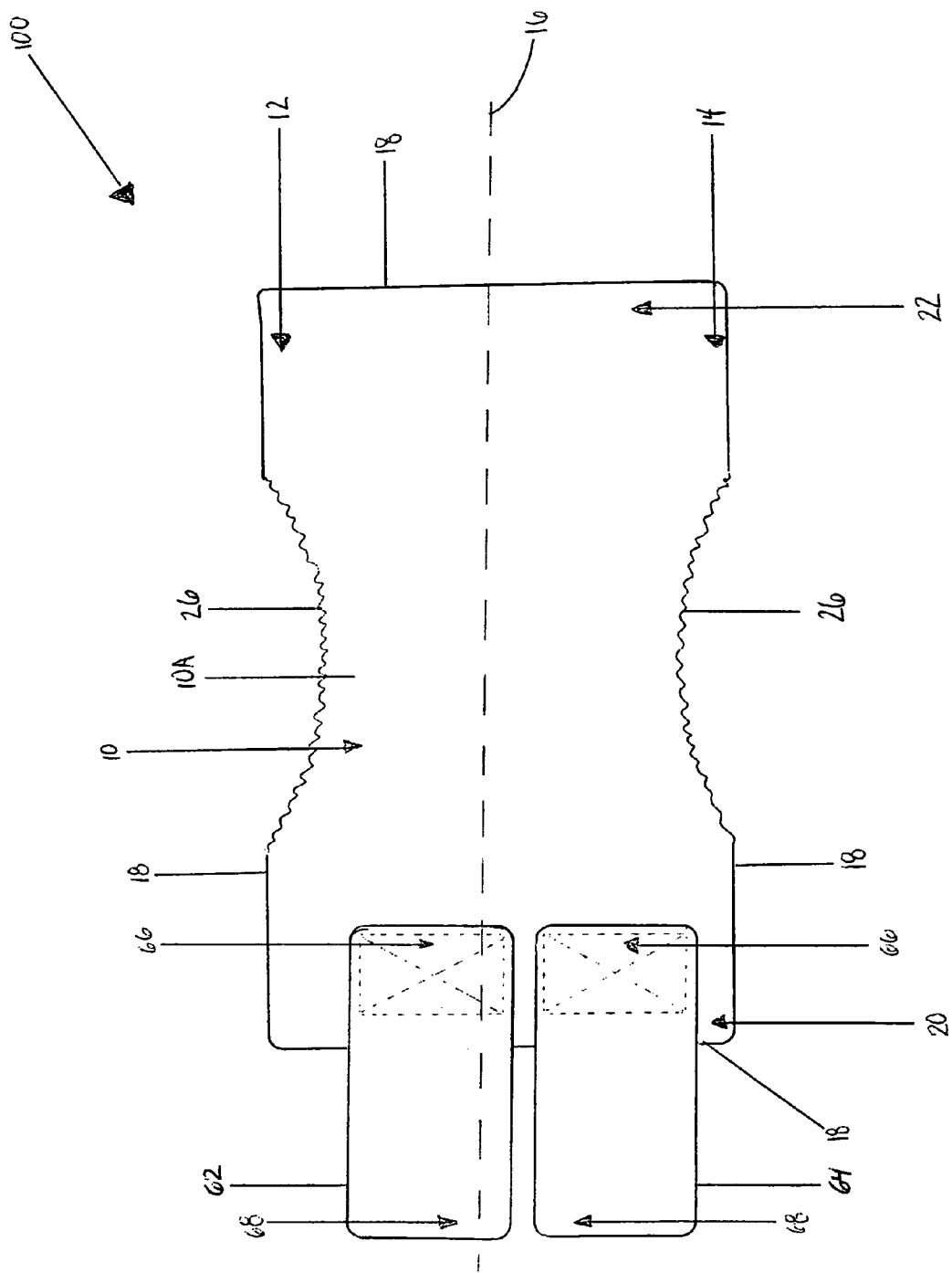
FIG. 4 of the drawings is a top plan view of an embodiment of a canine diaper showing, among other things, primary gathered regions on the front and back regions of the canine diaper, and at least two tabs secured to a first (i.e. top) surface of an outer liner, fabricated in accordance with the present invention.
Figure 5:
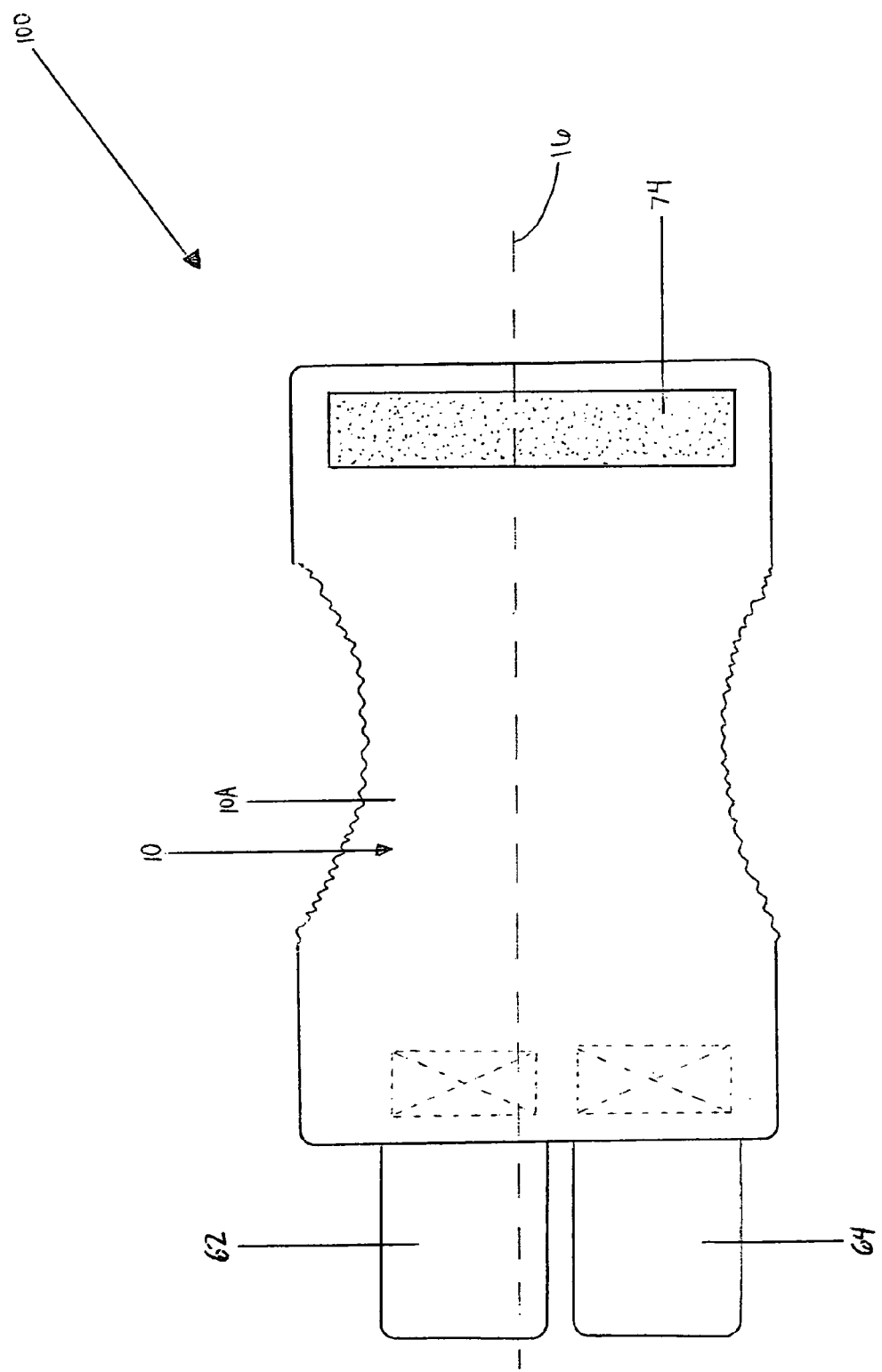
FIG. 5 of the drawings is a top plan view of an embodiment of a canine diaper showing, among other things, at least two tabs secured to a second (i.e. bottom) surface of an outer liner, fabricated in accordance with the present invention.
Figure 6:
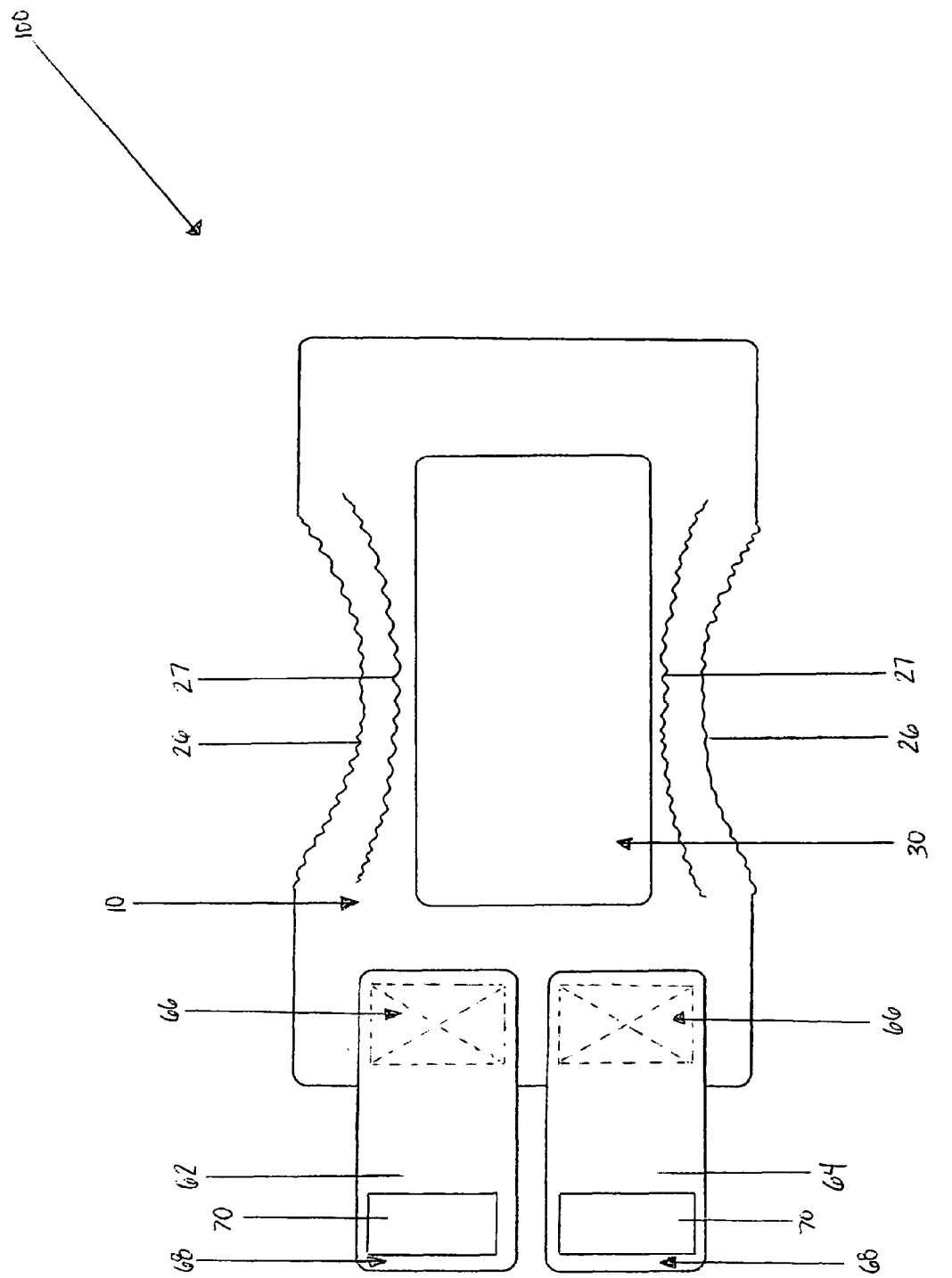
FIG. 6 of the drawings is a bottom plan view of an embodiment of a canine diaper showing, among other things, primary and second gathered regions and at least two tabs secured to a second (i.e. bottom) surface of an outer liner, fabricated in accordance with the present invention.

Likewise, FIGS. 1-7, collectively, show back region 14 of outer liner 10 as comprising a region of canine diaper 100 which is securable about at least a lower, rear portion of a torso of a dog. As can be seen in FIG. 7A, among others, it is also contemplated that back region 14 of outer liner 10 be securable substantially around a rear portion of a torso of a dog. As is shown in FIGS. 4-6, among others, it is preferred that back region 14 comprises primary gathered region 26 to, in turn, provide additional comfort and protection against leaks. In an attempt to provide even more comfort and protection against leaks, when each of front region 12 of outer liner 10 and back region 14 of outer liner 10 comprise primary gathered regions 26, outer liner 10 may further comprise at least one secondary gathered region 27 positioned within primary gathered regions 26 of front and back regions 12 and 14 of outer liner 10. As is shown in FIG. 6, preferably, at least one secondary gathered region 27 comprises two secondary gathered regions 27.

Longitudinal axis 16 is shown in the figures as extending along outer liner 10 of canine diaper 100 in a substantially parallel direction. It will be understood that longitudinal axis 16 is shown for purposes of illustration as referencing the relative position and/or direction of other members of canine diaper 100.

Figure 2B:
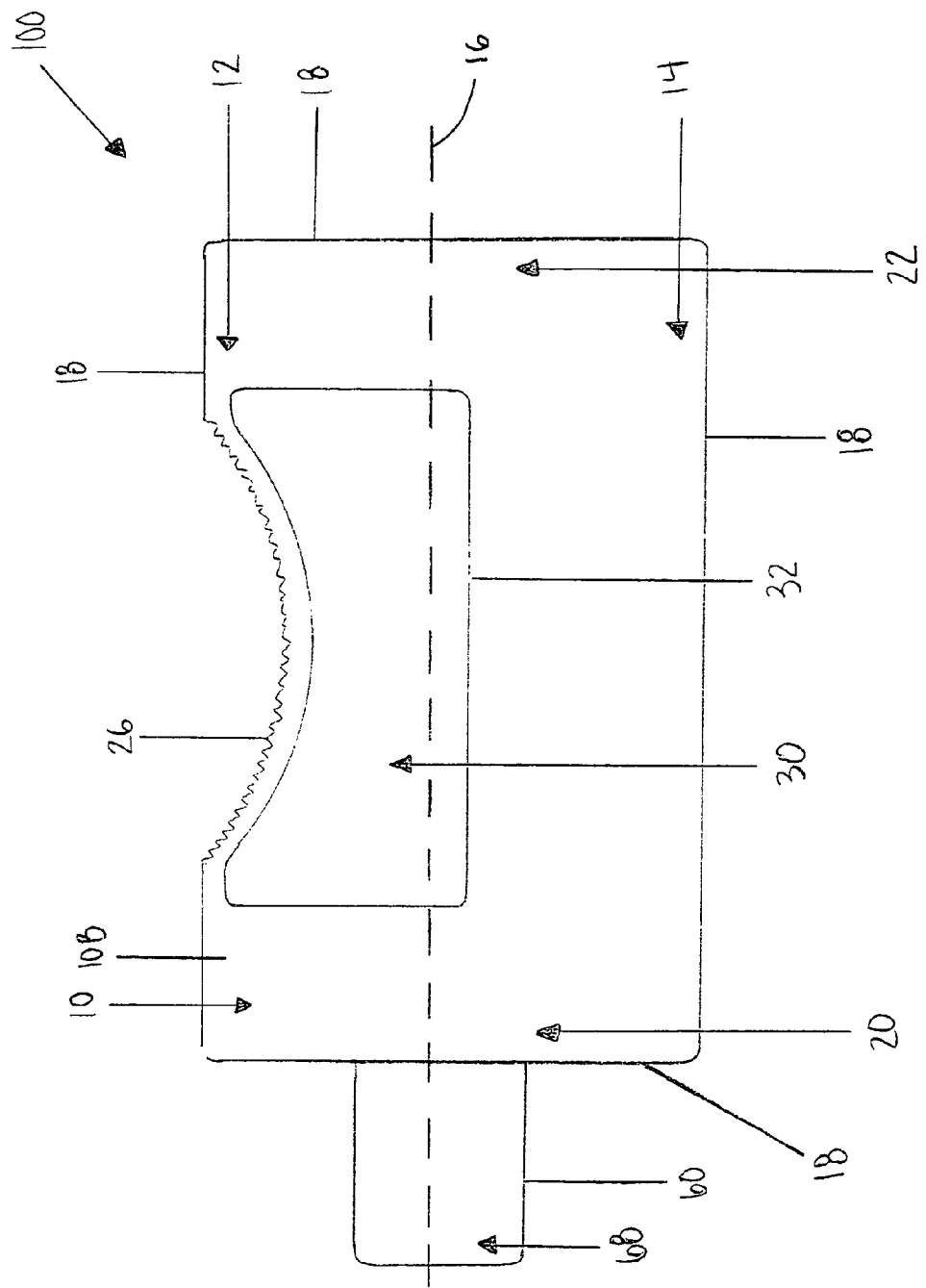

FIGS. 1 and 2A-2B, among others, show outer perimeter 18 of outer liner 10 as comprising the outermost edge of outer liner 10, which includes, among others, first end 20 and second end 22. While a substantially rectangular shape of outer perimeter 18 is shown, it will be understood that outer perimeter 18 may comprise any one of a number of different shapes and sizes, in order to accommodate the different shapes and sizes of a variety of dogs.

Figure 7A:
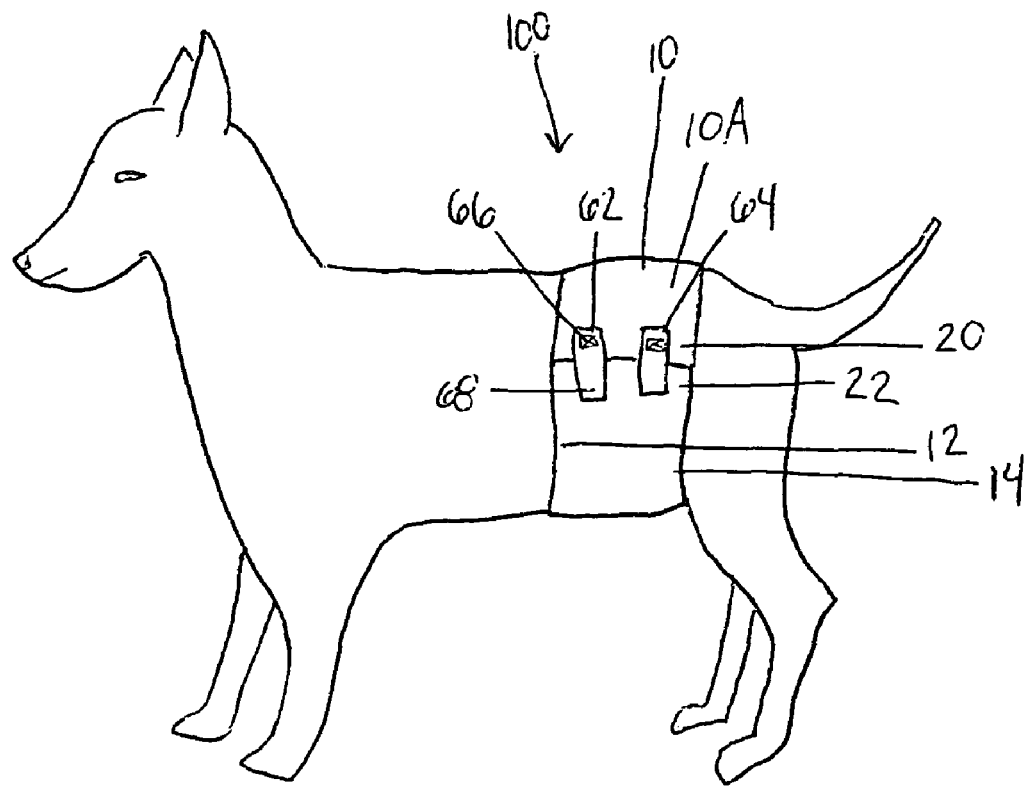
FIG. 7A of the drawings is a side perspective view of an embodiment of a canine diaper positioned substantially around a dog, wherein the first end of the outer liner mates with the second end of the outer liner, fabricated in accordance with the present invention.

First end 20 and second end 22 of outer perimeter 18 are positioned at substantially opposite ends of canine diaper 100, and extend in a substantially perpendicular orientation relative to longitudinal axis 16 of outer liner 10. FIG. 7A shows that in one embodiment, first end 20 mates with second end 22 when canine diaper 100 is secured around a torso of a dog via at least one tab 60.

Inner liner 30 is shown in FIGS. 2A-2B, among others, as comprising outer perimeter 32 which is secured to second surface 10B of outer liner 10 and within outer perimeter 18 of outer liner 10. While inner liner 30 is shown as comprising a substantially rectangular shape and a size which is less than the size of outer liner 10, inner liner 30 may comprise any one of a number of different shapes and sizes (including forward offset 2B), in order to accommodate the different shapes and sizes of a variety of dogs, so long as inner liner 30 is capable of being secured to outer liner 10 to enclose cavity 40 therebetween. As such, although not shown, it is also contemplated that inner liner 30 comprise the same size and shape as outer liner 10. Preferably, inner liner 30 is fabricated from a material which is substantially liquid permeable, flexible, and soft, in order to provide maximum comfort for a dog. It is also preferred that inner liner 30 is fabricated from an elastic, stretchable material. As such, inner liner 30 of canine diaper 100 may be fabricated from a fabric comprising, for example, cotton and/or spandex. However, it will be understood that the invention is not limited to a particular material of inner liner 30, and that inner liner 30 may be fabricated from any one of a number of natural and/or synthetic materials.

Cavity 40 is best shown in FIG. 3, as comprising a cavity positioned between outer liner 10 and inner liner 30 of canine diaper 100. Cavity 40 is enclosed by outer perimeter 32 of inner liner 30 and outer liner 10. As such, the size and shape of cavity 40 is defined by the size and shape of outer perimeter 32 of inner liner 30 and its securement to outer liner 10.

Absorbent core 50 is best shown in FIG. 3, as being retained within cavity 40. Absorbent core 50 comprises a highly absorbent material capable of absorbing and retaining liquid waste, such as urine, excreted by a dog. As such, absorbent core 50 may comprise an absorbent type sponge, foam, padding, and/or chemical, or other highly absorbent materials known to those skilled in the art. Although not shown, it is also contemplated that absorbent core 50 be removable from cavity 40 for purposes of washing and reusing. In addition, although not shown in the figures, it is preferred that absorbent core 50 may comprise any one of a number of additives which improve and/or preserve the integrity of canine diaper 100. For example, absorbent core 50 may comprise a chemical indicator which changes from a substantially colorless state to a highly colored state upon exposure to urine to, in turn, apprise an observer that the canine diaper has been soiled. Absorbent core 50 may also include an odor-resistant material, such as an anti-bacillus polymer, or other odor-resistant material known to those skilled in the art. In addition, absorbent core 50 may comprise a urine odor neutralizer which neutralizes the scent of canine urine. Furthermore, absorbent core 50 may comprise an aromatically-pleasing, odor-generating organic ester which is capable of masking or covering up a natural scent of male canine reproductive organs. Such odor resistors, odor neutralizers, odor generators, and/or esters are impregnated within the diaper to better hide any unpleasant aromas commonly associated with a dog.

As is shown collectively in FIGS. 1, 2A-2B, and 4-7, among others, at least one tab 60 is substantially parallel to longitudinal axis 16 of outer liner 10, and generally comprises first securement region 66 and second securement region 68. As FIGS. 4-7, collectively, illustrate, it is preferred that at least one tab 60 comprises at least two tabs, such as first tab 62 and second tab 64. In this embodiment, each of first tab 62 and second tab 64 comprise first securement region 66 and second securement region 68.

At least a portion of first securement region 66 of at least one tab 60 is secured directly to first end 20 of outer liner 10 and within outer perimeter 18 of outer liner 10. First securement region 66 may either be secured to first surface 10A of outer liner 10, as is shown in FIGS. 1, 2A-2B, and 4, or, alternatively, to second surface 10B of outer liner 10, as is shown in FIGS. 5 and 6. Preferably, all of first securement region 66 of at least one tab 60 is secured directly to first end 20 of outer liner 10 and within outer perimeter 18 of outer liner 10. First securement region 66 is secured to first end 20 via any one of a number of different securing means known to those with ordinary skill in the art, such as, but not limited to, fusing, sewing, fasteners, various tapes, and adhesives—just to name a few.

At least a portion of second securement region 68 is releasably secured to second end 22 of outer liner 10 to, in turn, associate first end 20 of outer liner 10 with second end 22 of outer liner 10, thereby securing outer liner 10 and, in turn, canine diaper 100, substantially around a torso of a dog. As is shown in FIG. 6, preferably, second securement region 68 is releasably secured to second end 22 via fastener 70. Fastener 70 may comprise any one of a number of fastening means, such as, but not limited to, adhesive, snaps, buttons, and/or a plurality of hooks which releasably secures to a plurality of loops 74 on second end 22 of outer liner 10, as is shown in FIG. 5. However, it will be understood that second securement region 68 may be releasably secured to second end 22 via any one of a number of different releasably securing means known to those with ordinary skill in the art.

Figure 7B:
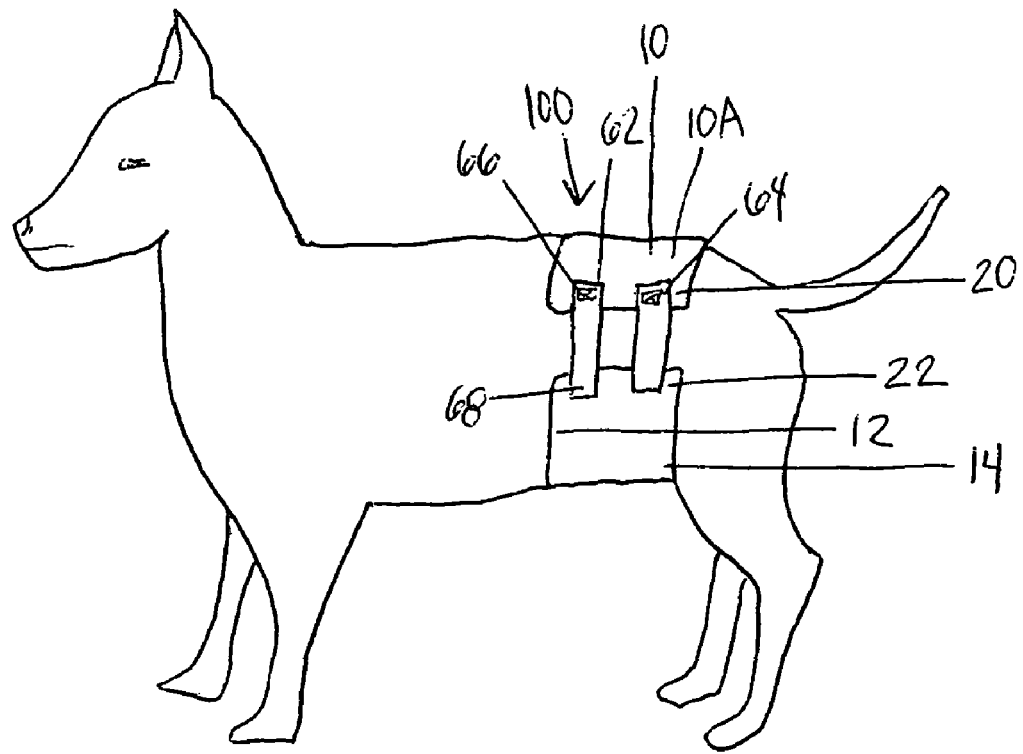
FIG. 7B of the drawings is a side perspective view of an embodiment of a canine diaper positioned substantially around a dog, fabricated in accordance with the present invention.

Canine diaper 100 is positioned onto a dog by wrapping canine diaper 100 around a rear portion of a torso of a dog, such that second surface 10B of outer liner 10 and inner liner 30 is positioned inward and in contact with the dog's genital region, and first surface 10A of outer liner 10 is positioned outward and away from the dog, as is shown in FIGS. 7A and 7B. At least one tab 60 is then releasably secured to second end 22 of outer liner 10 which associates first end 20 of outer liner 10 with second end 22 of outer liner 10, thereby securing outer liner 10 and, in turn, canine diaper 100, substantially around the dog.

The foregoing description merely explains and illustrates the invention and the invention is not limited thereto except insofar as the appended claims are so limited, as those skilled in the art who have the disclosure before them will be able to make modifications without departing the scope of the invention.

What is claimed is:

1. A canine diaper, comprising:
an outer liner, wherein the outer liner is substantially liquid impermeable, and wherein the outer liner comprises:
   a front region, wherein the front region of the outer liner is securable about a front portion of a torso of a dog;
   a back region, wherein the back region of the outer liner is securable about a rear portion of a torso of a dog;
   a longitudinal axis; and
   an outer perimeter which includes a first end and a second end;
an inner liner, wherein the inner liner is substantially liquid permeable, and wherein the inner liner comprises an outer perimeter secured to the outer liner to enclose a cavity therebetween;
a cavity positioned between the inner liner and the outer liner;
an absorbent core, wherein the absorbent core is retained within the cavity; and
at least one tab, wherein the at least one tab includes a length and a width, wherein the length is greater in dimension than the width, and further wherein the length that is substantially parallel to the longitudinal axis of the outer liner, and wherein the at least one tab comprises:
   a first securement region, wherein at least a portion of the first securement region of the tab is secured directly to the first end of the outer liner; and
   a second securement region, wherein the second securement region is releasably secured to the second end of the outer liner to, in turn, associate the first end of the outer liner with the second end of the outer liner, thereby securing the canine diaper substantially around a torso of a dog.

2. The canine diaper according to claim 1, wherein the at least one tab comprises at least two tabs.

3. The canine diaper according to claim 1, wherein the at least one tab consists of two tabs.

4. The canine diaper according to claim 1, wherein all of the first securement region of the at least one tab is secured directly to the first end of the outer liner and within the outer perimeter of the outer liner.

5. The canine diaper according to claim 1, wherein the first end of the outer liner mates with the second end of the outer liner when the canine diaper is secured around a torso of a dog via the at least one tab.

6. The canine diaper according to claim 1, wherein the second securement region of the at least one tab comprises a fastener which releasably secures the second securement region of the at least one tab to the second end of the outer liner.

7. The canine diaper according to claim 1, wherein the second securement region of the at least one tab comprises a plurality of hooks, and wherein the second end of the outer liner further comprises a plurality of loops, and wherein the plurality of hooks of the second securement region of the at least one tab releasably secures to the plurality of loops of the second end of the outer liner.

8. The canine diaper according to claim 1, wherein at least one of the front region of the outer liner and the back region of the outer liner comprises a gathered region.

9. The canine diaper according to claim 1, wherein each of the front region of the outer liner and the back region of the outer liner comprise a primary gathered region, and wherein the outer liner further comprises two secondary gathered regions positioned within the primary gathered regions.

10. The canine diaper according to claim 1, wherein the absorbent core comprises a chemical indicator which changes from a substantially colorless state to a highly colored state upon exposure to urine to, in turn, apprise an observer that the canine diaper has been soiled.

11. The canine diaper according to claim 1, wherein the absorbent core comprises a urine odor neutralizer.

12. A disposable canine diaper, comprising:
an outer liner, wherein the outer liner is substantially liquid impermeable, and wherein the outer liner comprises:
a front region, wherein the front region of the outer liner is securable about a front portion of a torso of a dog;
a back region, wherein the back region of the outer liner is securable about a rear portion of a torso of a dog;
a longitudinal axis; and
an outer perimeter which includes a first end and a second end;
an inner liner, wherein the inner liner is substantially liquid permeable, and wherein the inner liner comprises an outer perimeter secured to the outer liner to enclose a cavity therebetween;
a cavity positioned between the inner liner and the outer liner;
an absorbent core, wherein the absorbent core is retained within the cavity; and
at least two tabs, wherein each one of the at least two tabs includes a length and a width, wherein the length is greater in dimension than the width, and further wherein the length is substantially parallel to the longitudinal axis of the outer liner, and wherein each of the at least two tabs comprises:
a first securement region, wherein at least a portion of the first securement region of each of the at least two tabs is secured directly to the first end of the outer liner; and
a second securement region, wherein the second securement region of each of the at least two tabs is releasably secured to the second end of the outer liner to, in turn, associate the first end of the outer liner to the second end of the outer liner, thereby securing the canine diaper substantially around a torso of a dog.

13. The canine diaper according to claim 12, wherein all of the first securement region of each of the at least two tabs is secured directly to the first end of the outer liner and within the outer perimeter of the outer liner.

14. The canine diaper according to claim 12, wherein the first end of the outer liner mates with the second end of the outer liner when the canine diaper is secured around a torso of a dog via the at least two tabs.

15. The canine diaper according to claim 12, wherein the second securement region of each of the at least two tabs comprises a fastener which releasably secures the second securement region of each of the at least two tabs to the second end of the outer liner.

16. The canine diaper according to claim 12, wherein the second securement region of each of the at least two tabs comprises a plurality of hooks, and wherein the second end of the outer liner further comprises a plurality of loops, and wherein the plurality of hooks of the second securement region of each of the at least two tabs releasably secures to the plurality of loops of the second end of the outer liner.

17. The canine diaper according to claim 12, wherein each of the front region of the outer liner and the back region of the outer liner comprise a primary gathered region, and wherein the outer liner further comprises two secondary gathered regions positioned within the primary gathered regions.

18. The canine diaper according to claim 12, wherein the absorbent core comprises at least one of the group comprising:
a chemical indicator which changes from a substantially colorless state to a highly colored state upon exposure to urine to, in turn, apprise an observer that the canine diaper has been soiled;
a urine odor neutralizer; and
an aromatically-pleasing, odor-generating organic ester which masks a natural scent of male canine reproductive organs.

19. A disposable canine diaper, consisting of:
an outer liner, wherein the outer liner is substantially liquid impermeable, and wherein the outer liner comprises:
a front region, wherein the front region of the outer liner is securable about a front portion of a torso of a dog, and wherein the front region of the outer liner comprises a primary gathered region;
a back region, wherein the back region of the outer liner is securable about a rear portion of a torso of a dog, and wherein the back region of the outer liner comprises a primary gathered region;
two secondary gathered regions positioned within the primary gathered regions;
a longitudinal axis; and
an outer perimeter which includes a first end and a second end, wherein the first end of the outer liner mates with the second end of the outer liner when the outer liner is secured around a torso of a dog;
an inner liner, wherein the inner liner is substantially liquid permeable, and wherein the inner liner comprises an outer perimeter secured to the outer liner to enclose a cavity therebetween;
a cavity positioned between the inner liner and the outer liner;
an absorbent core, wherein the absorbent core is retained within the cavity, and wherein the absorbent core comprises at least one of the group comprising:
a chemical indicator which changes from a substantially colorless state to a highly colored state upon exposure to urine to, in turn, apprise an observer that the canine diaper has been soiled;
a urine odor neutralizer; and an aromatically-pleasing, odor-generating organic ester which masks a natural scent of male canine reproductive organs; and at least two tabs, wherein each of the at least two tabs is substantially parallel to the longitudinal axis of the outer liner, and wherein each of the at least two tabs comprises:
 a first securement region, wherein all of the first securement region of each of the at least two tabs is secured directly to the first end of the outer liner and within the outer perimeter of the outer liner; and
 a second securement region, wherein the second securement region of each of the at least two tabs comprises a fastener which releasably secures the second securement region of each of the at least two tabs to the second end of the outer liner to, in turn, associate the first end of the outer liner with the second end of the outer liner, thereby securing the canine diaper substantially around a torso of a dog.

20. A canine diaper, comprising:
an outer liner, wherein the outer liner is substantially liquid impermeable, and wherein the outer liner comprises:
 a front region, wherein the front region of the outer liner is securable about a front portion of a torso of a dog;
 a back region, wherein the back region of the outer liner is securable about a rear portion of a torso of a dog;
 a longitudinal axis; and
 an outer perimeter which includes a first end and a second end;

an inner liner, wherein the inner liner is substantially liquid permeable, and wherein the inner liner comprises an outer perimeter secured to the outer liner to enclose a cavity therebetween;

a cavity positioned between the inner liner and the outer liner;

an absorbent core, wherein the absorbent core is retained within the cavity, and wherein the absorbent core comprises an aromatically-pleasing, odor-generating organic ester which masks a natural scent of male canine reproductive organs; and at least one tab, wherein the at least one tab is substantially parallel to the longitudinal axis of the outer liner, and wherein the at least one tab comprises:
 a first securement region, wherein at least a portion of the first securement region of the tab is secured directly to the first end of the outer liner; and
 a second securement region, wherein the second securement region is releasably secured to the second end of the outer liner to, in turn, associate the first end of the outer liner with the second end of the outer liner, thereby securing the canine diaper substantially around a torso of a dog.

* * * * *